(12) United States Patent
Perrot et al.

(10) Patent No.: US 9,592,057 B2
(45) Date of Patent: Mar. 14, 2017

(54) COMPRESSION, BANDING AND PERCUTANEOUS AIRWAY LIGATION OF EMPHYSEMATOUS LUNG TISSUE

(71) Applicant: Boston Scientific Scimed, Inc., Maple Grove, MN (US)

(72) Inventors: Alexandra Perrot, Cambridge, MA (US); Mark Wood, Shrewsbury, MA (US); Jon T. McIntyre, Newton, MA (US); Claude Clerc, Marlborough, MA (US); Gary Leanna, Holden, MA (US); Michael S. H. Chu, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 126 days.

(21) Appl. No.: 14/260,951

(22) Filed: Apr. 24, 2014

(65) Prior Publication Data

US 2014/0236185 A1   Aug. 21, 2014

Related U.S. Application Data

(63) Continuation of application No. 12/209,591, filed on Sep. 12, 2008, now Pat. No. 8,728,093.

(60) Provisional application No. 60/973,269, filed on Sep. 18, 2007.

(51) Int. Cl.
*A61B 17/10* (2006.01)
*A61B 17/12* (2006.01)
*A61B 17/04* (2006.01)

(52) U.S. Cl.
CPC .. *A61B 17/12013* (2013.01); *A61B 17/12009* (2013.01); *A61B 2017/0419* (2013.01); *A61B 2017/12018* (2013.01)

(58) Field of Classification Search
CPC ........ A61B 17/12009; A61B 17/12013; A61B 2017/12018
See application file for complete search history.

(56) References Cited

U.S. PATENT DOCUMENTS 6,152,936 A  * 11/2000 Christy ............. A61B 17/0483
                                                           606/139
6,514,290 B1 *  2/2003 Loomas ................ A61F 2/0063
                                                           600/37

* cited by examiner

*Primary Examiner* — Gregory Anderson
(74) *Attorney, Agent, or Firm* — Fay Kaplun & Marcin, LLP

(57) ABSTRACT

A lung volume reduction system includes a percutaneously, laparoscopically or thorocospically insertable delivery element comprising a control end which remains outside the body and an insertion end which, when in an operative position, is adjacent to an external surface of a target portion of a lung and a constriction element deployable from the distal end of the delivery element to apply compressive force to an external surface of the target portion of the lung to constrict at least one airway therein and collapse the target portion of the lung.

18 Claims, 3 Drawing Sheets

COMPRESSION, BANDING AND PERCUTANEOUS AIRWAY LIGATION OF EMPHYSEMATOUS LUNG TISSUE

PRIORITY CLAIM

The present application is a Continuation of pending U.S. patent application Ser. No. 12/209,591 filed on Sep. 12, 2008, now U.S. Pat. No. 8,728,093; which claims the priority to the U.S. Provisional Application Ser. No. 60/973,269 filed on Sep. 18, 2007. The entire disclosure of these applications/patents are expressly incorporated herein by reference.

BACKGROUND

Emphysema, a progressive, often incurable disease of the lungs often results from chronic infection or irritation of the bronchial tubes. As the bronchial tubes become irritated, some of the airways may be obstructed, trapping air in the alveoli. As this process continues, the alveoli become enlarged and exchange oxygen for carbon dioxide less efficiently. Furthermore, these expanded portions of the lungs may compress adjacent healthy portions of the lungs interfering with their functioning.

Lung volume reduction surgery (LVRS) is one treatment used to relieve the symptoms of emphysema by removing diseased portions of the lungs to create more room for the remaining healthy portions. Although LVRS has been shown to improve pulmonary function and the survival rate in selected patients the complications associated with such major, open surgical procedures make LVRS unsuitable for certain patients.

Minimally invasive procedures have also been employed to achieve results similar to those of LVRS while minimizing the associated complications. These less invasive procedures generally involve depositing in the lungs devices that restrict the flow of air to the diseased portions of the lungs. Often, a bronchoscope or laparoscope is used to deliver the devices obviating the need for surgical openings into the chest cavity.

SUMMARY OF THE INVENTION

The present invention is directed to a lung volume reduction system comprising a percutaneously insertable delivery element comprising a control end which remains outside the body and an insertion end which, when in an operative position, is adjacent to an external surface of a target portion of a lung and a constriction element deployable from the distal end of the delivery element to apply compressive force to an external surface of the target portion of the lung to constrict at least one airway therein and collapse the target portion of the lung. As would be understood by those skilled in the art, this collapsed condition may, if desired, be continued for a period of time sufficient to necrose the collapsed portion of tissue permanently eliminating the inefficiencies of this diseased portion of tissue from the lung.

DETAILED DESCRIPTION

Figure 1:
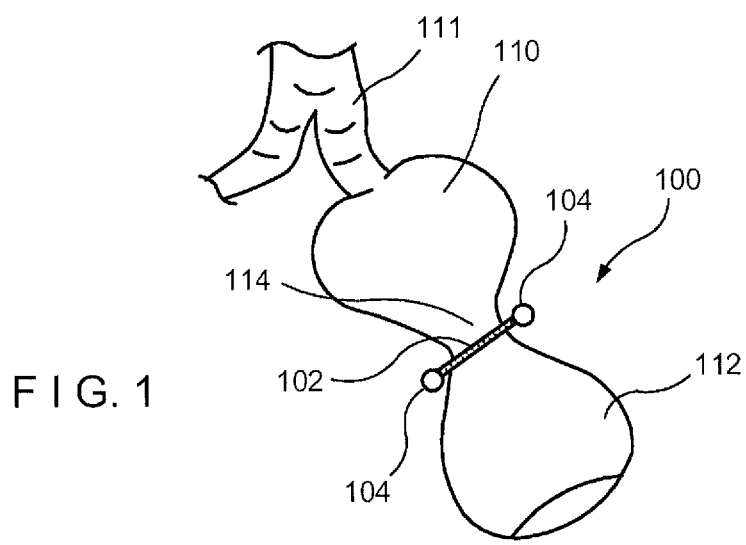
FIG. 1 is a diagram showing an embodiment of a device used to collapse a lung according to the present invention.

The present invention may be further understood with reference to the following description and the appended drawings, wherein like elements are referred to with the same reference numerals. The present invention relates to devices for treatment of emphysema and more specifically relates to devices for reducing the size of diseased lung tissue to improve the functioning of remaining healthy tissue.

According to embodiments of the present invention, a percutaneous procedure is employed to access diseased regions of the lungs and to deploy thereto devices to reduce the volume of the diseased tissue increasing the efficiency of the healthy tissue.

The exemplary embodiments of the present invention comprise procedures employing banding and/or compression devices to reduce the volume of emphysematous tissue. Depending on the details of a particular case, these devices may be deployed from outside or within the lung. The exemplary devices according to the present invention isolate targeted tissue from portions of the lungs upstream thereof to reduce the volume by preventing further influx of air. Other devices according to the invention compress the target tissue to decrease its volume.

FIG. 1 shows an exemplary embodiment of a system 100 for collapsing a target portion of the lung by clamping or pinching a lobe of the lung. The system 100 includes a rivet or peg 102 which is placed into the thoracic cavity and inserted through a target lobe 112 of a lung 110. The rivet or peg 102 is preferably inserted minimally invasively through, for example, a laparoscope or thoracoscope introduced between the ribs into the thoracic cavity via a small incision with a distal end of the peg 102 being inserted through the target lobe 112 and secured in place by tightening to desired dimensions using conventional locking mechanisms or anchoring members 104. For example, the system 100 may include a tube of substantially circular cross-section through which suction may be applied to draw a portion of lung tissue into the tube after which an elastic ligator may be pushed off the distal end of the tube so that the elastic ligator contracts to constrict the portion of the lung which has been drawn into the tube. Alternatively, as would be understood by those skilled in the art, a tie wrap may be placed around a target portion of the lung and then an end of the tie wrap may be drawn out to tighten the tie wrap around the target portion and constrict the target portion of tissue. After the distal end of the peg 102 has passed through the target lobe 112 to a desired position on a side opposite a point of insertion into the target lobe 112, a first anchor member 104 is attached to or, alternatively, deployed from, the distal end of the peg 102 and the target lobe 112 is compressed against the first anchor member 104 to a desired degree. The distal end of the peg 102 is prevented from being pulled back into the interior of the target lobe 112 by the first anchor member 104 which engages an exterior of the target lobe 112. Compressing the target lobe 112 against the distal end of the peg 102 reduces the volume of the target lobe 112 by creating a neck region 114 of reduced cross-sectional area. When a desired amount of compression of the target lobe 112 has been achieved, a second anchor member 104 is deployed from a proximal portion of the peg 102 to maintain the desired amount of compression of the target lobe 112. After the second anchor member 104 has been deployed, any excess length of the peg 102 may be trimmed away and the laparoscope may be removed. Those skilled in the art will understand that the peg 102 and the anchoring members 104 are preferably adapted to engage portions of the exterior of the target lobe 112 large enough to hold the anchoring members 104 in position against forces applied thereto during respiration and as the patient moves about.

Constriction by the peg 102 collapses the bronchial passages in the neck region 114 preventing the passage of air to the target lobe 112 to inflate the alveoli contained therein. Thus surrounding healthy portions of the lung may inflate more freely and carry out the exchanges of gases more efficiently. Over time, the target lobe 112 will necrose because of the constriction further reducing its volume. In an alternative example, a peg 102 may be placed within a target lobe 112 and anchored across a target bronchial passage therein to prevent air flow only to that portion of the target lobe 112 served by the target bronchial passage.

Figure 2:
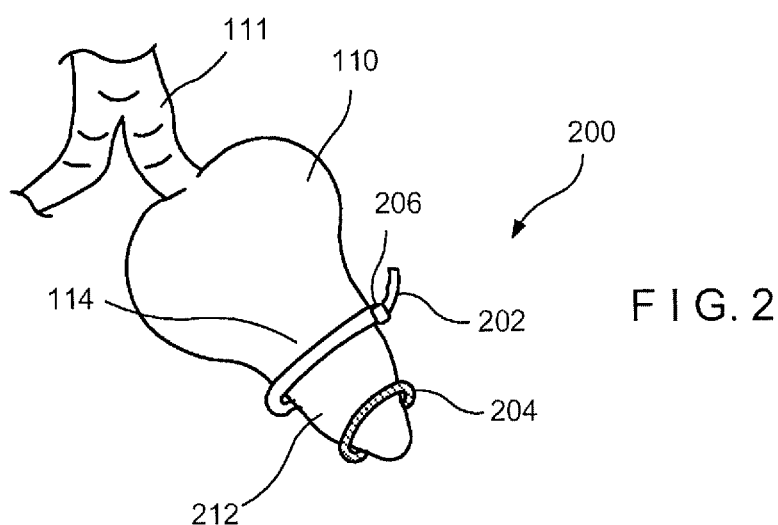
FIG. 2 is a diagram showing another embodiment of a device used to collapse a lung using a mechanical tie according to the present invention.
Figure 3:
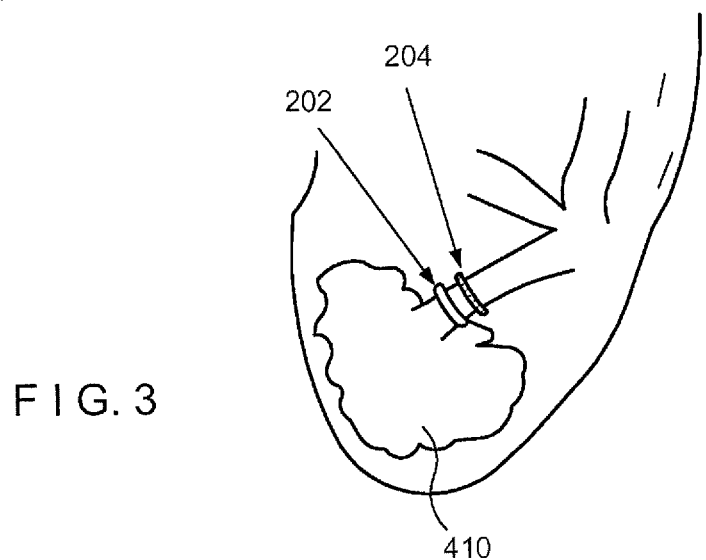
FIG. 3 is a diagram showing an embodiment of a percutaneous airway lung ligation band according to the present invention, during deployment.
Figure 4:
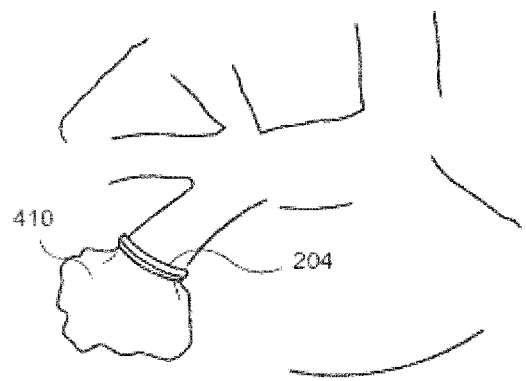
FIG. 4 is a diagram showing the lung ligation band of FIG. 3 after deployment.

A system 200 to reduce lung volume according to a second embodiment of the invention is shown in FIGS. 2-4. According to this exemplary embodiment, a mechanical element such as a tie or a clamp 202 is placed around a target portion 212 of the lung 110 to separate the target portion 212 from upstream portions of the lung 110 to collapse the target portion 212. The tie or clamp 202 is applied around the lung 110 to compress the target portion 212 of the lung 110 downstream of an airway branch 111. As with the peg 102 of the system 100, the tie or clamp 202 is preferably inserted into the thoracic cavity through a minimally invasive method, such as through a laparoscopic procedure, and may be secured in place by tightening to the correct dimensions using a conventional locking mechanism 206. Alternatively, the tie or clamp 202 may be replaced, or supplemented, by an elastic band 204 or a shape memory element which, when released around a target portion of the target lobe 212 will contract without the need for a locking mechanism to apply compression thereto. For example, the constriction element may be a loop of a shape memory material such as Nitinol formed so that, when deployed it reverts to a memorized shape with a reduced diameter. The elastic bands 204, or other type of compression element, may also be applied through a laparoscopic procedure or other minimally invasive approach. For example, one or more elastic bands 204 may be disposed around a cylinder into which a portion of the target lobe 212 is drawn (e.g., by suction applied thereto) at which point a first one of the elastic bands 204 may be released (e.g., by drawing a trigger line attached thereto) to contract around the portion of the target lobe 212 adjacent to a distal end of the cylinder.

As shown in FIGS. 3 and 4 the system 200 collapses a target portion 410 of the lung by isolating it from remaining portions of lung to cut-off the supply of air thereto. A constriction element (e.g., a tie or clamp 202 or an elastic band 204) is deployed from a delivery element onto the airway, so that the passage of air is blocked. For example, a tube such as an endoscope (not shown) may be inserted between the ribs into the thoracic cavity via an incision with one or more constriction elements received around a distal end of the endoscope. The distal end of the endoscope preferably includes a hollow chamber into which the target portion 410 may be drawn (e.g., under suction) so that the distal end of the endoscope and the constriction element received thereon surrounds the target portion 410. In this position, the constriction element is moved off of the distal end of the endoscope so that it encircles a portion of the lung upstream of the target portion 410. When the constriction element is an elastic band 204, the band 204 tightens immediately after it passes off of the distal end of the endoscope to constrict the lung tissue therewithin, preventing the flow of air therethrough. Ties or clamps 202 deployed in this manner are then tightened around the lung tissue to prevent the flow of air to the target portion 410. Those skilled in the art will understand that these constriction elements may be formed of bioabsorbable materials which are preferably selected to retain their form until after a time required to achieve a desired therapeutic effect has elapsed. For example, such a bioabsorbably constriction element may be selected to remain in position, as shown in FIG. 4, until the target portion 410 has completely collapsed and the flow passage(s) thereto are sealed. As would be understood by those skilled in the art, the system 200 may deploy the ligating bands 204 using a mechanism substantially similar to an elastic band ligating system for treating esophageal varices as described, for example, in U.S. Pat. No. RE36,629 issued to Zaslaysky, et al., Mar. 28, 2000, the entire disclosure of which is hereby incorporated by reference.

Figure 5:
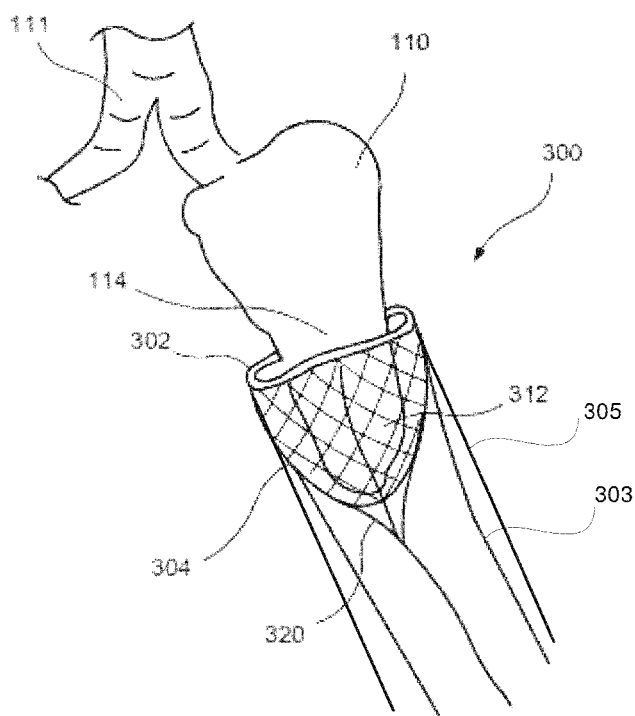
FIG. 5 is a diagram showing a further embodiment of a device used to collapse a desired portion of lung using an elastic bag, according to the present invention.

As shown in FIG. 5, a system 300 according to an additional embodiment of the lung reduction system according to the invention includes an elastic bag or sock 304 which is stretched for placement around a portion of a target lobe 312 of the lung 110. Upon release, the bag 304 contracts to apply a compressive force to a portion of a surface of the target lobe 312 of the lung 110 larger than that affected by the clamp 202 or the ligating band 204. That is, the open end of the bag 304 constricts air flow into the target lobe 312 of the lung 110 as in the prior embodiments while the remaining portions of the bag 304 actively compress the target lobe 312. As would be understood by those skilled in the art, the bag 304 may be designed to apply a compressive force which is substantially equal across the surface area of the target lobe 312 with which it is in contact. Alternatively, the bag 304 may be designed to apply a force which varies over the surface area. For example, the bag 304 may be designed to apply a force which is a maximum along a line which, when the bag 304 is in a desired position on the target portion of the lobe 312, is furthest upstream on the lobe 312 (e.g., at the open end of the bag 304) or to cause the collapse of portions of the target lobe 312 in a desired sequence. In the exemplary embodiment, the bag or sock 304 comprises a band 302 adapted to retain the device in place on the target portion of the lung 110. For example, the band 302 may have an inner surface shaped to grasp the tissue of the lung and prevent it from slipping off the target lobe 312. The band 302 may, for example, be made of an elastic material, or may be tightened mechanically as desired in a manner similar to that described above.

The bag or sock 304 according to the present invention is preferably made of a bioabsorbable material such as polyurethane or lycra so that it does not have to be removed after the compressed portion of the target lobe 12 has necrosed to a desired level. As with other embodiments of the present invention, the bag or sock 304 is designed to be placed using minimally invasive techniques. Specifically, the bag or sock 304 can be inserted into the body through a small incision or port on an elongated retractor device 303. An insertion device 305 can be seen in FIG. 5. The distal end of the retractor is generally maintained in a closed condition so that the sock 304 can be placed thereover to keep the retractor in a low profile. When the sock 304 is placed adjacent to the target lobe 312, a handle of the retractor is activated to expand the sock 304 using, for example, three or more arms 320 for ease of placement over the target lobe 312. The handle of the retractor may be attached, via known means, to the plurality of arms 320 so that, upon activation, the arms extend radially outward from the device. Once the sock 304 is placed in the desired location, the arms of the retractor device may be retracted in order to release the hold on the sock 304. The arms 320 of the retractor can then be removed from the body in a closed position in order to minimize trauma to the patient.

Figure 6:
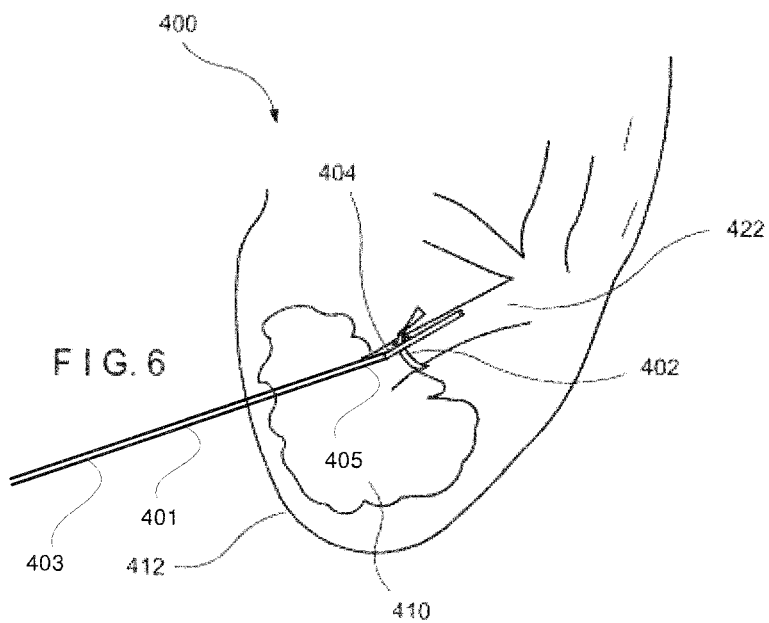
FIG. 6 is a diagram showing a further embodiment of a device used to collapse a desired portion of lung according to the present invention.

As shown with respect to FIG. 6, the exemplary lung reduction system 400 is designed to be performed percutaneously to treat a target portion or lobe 410 of a lung 412. Those skilled in the art will understand that the percutaneous method may be used in conjunction with an imaging modality, such as, for example fluoroscopy. Alternately, a laparoscopic procedure may be employed to facilitate visual observation during the procedure. As another possibility, the procedure may be performed thoracospically, via VATS or via the use of SPY fiber technology in one of the working channels of the scope, as those skilled in the art will understand. In this embodiment, the delivery element 401 comprises a percutaneous axial member 404 (e.g., a flexible tube) used to deliver an elastic band 402 or other constriction element to an airway 422 such as a bronchial tube. A distal end 405 of the axial member 404 is introduced into the body and placed adjacent to the airway 422 to be treated while a proximal end 403 of the percutaneous axial member 404 remains outside the body for manipulation by a user for positioning of the distal end over a desired target portion of the lung 412.

As would be understood by those skilled in the art, a conventional mechanism, similar to those used for band ligation of esophageal varices, may be used to deploy the elastic band 402 from the axial member 404, so that the elastic band 402 wraps around and is anchored to a portion of the air passage 422 which had previously been drawn into the axial member 404. For example, as described above in regard to the embodiment of FIG. 2, a cord extending along the length of the percutaneous rod 404 may be used to pull one elastic band 402 at a time off the axial member 404, and release it over the air passage 422. In another embodiment, a longitudinal member may extend along the length of the axial member 404 so that the longitudinal member may slide along the length thereof to individually release the elastic bands 402. Alternatively, the elastic band 402 may have a length that can be varied by the user, so that it can be elongated to pass over the hyperinflated portion of the lung 410, and then shortened to tighten around the air passage 422. The elastic band 402, when released over the air passage 422, constricts to cut off air-flow to the hyperinflated target portion or lobe 410 from the rest of the lung 412 leading to necrosis of this target portion or lobe 410. The elastic band 402 is preferably formed of biodegradable material so that it may remain in place for a substantial amount of time to prevent re-inflation of the target lobe or portion 410', by blocking the air passing through the airway 422. As would be understood by those skilled in the art, the material of the elastic band 402 is selected to remain in position for a length of time sufficient to collapse the target lobe 410' to a desired level. In cases where the elastic band is not biodegradable, an additional procedure may be performed to remove the band 402 from the body after the desired level of collapse has been achieved.

Figure 7:
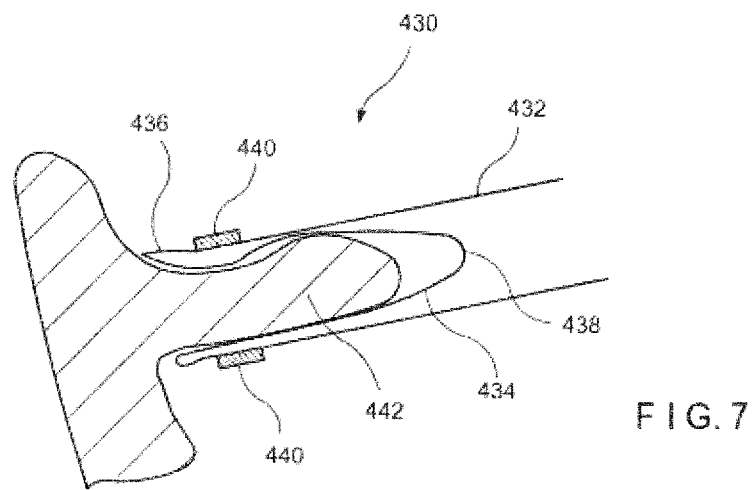
FIG. 7 shows an apparatus according to a further embodiment of the invention for collapsing a desired portion of lung.

As shown in FIG. 7, a system 430 similar to that described above in regard to FIGS. 3 and 4 may be used to deploy a bag or sock similar to those described above in regard to FIG. 5. The system 430 includes an axial member 432 with a bag or sock member 434 with an open end 436 wrapped around the distal end of the axial member 432. The closed end 438 of the sock member 434 extends within a lumen of the axial member 432 while an elastic member 440 extending around the open end 436 holds the sock member 434 to the distal end of the axial member 432. After being advanced to a location adjacent a target portion 442 of lung to be treated in the same manner described above, the target portion 442 of lung is aspirated into the distal end of the axial member 432 via the application of suction or the manipulation of a grasper through the lumen of the axial member 432 and the elastic member 440 is released from the distal end of the axial member 432 to constrict around the target portion 442 maintaining the sock member 434 in position over the target portion 442.

The present invention has been described with reference to specific exemplary embodiments. Those skilled in the art will understand that changes may be made in details, particularly in matters of shape, size, material and arrangement of parts without departing from the teaching of the invention. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A lung volume reduction system, comprising:
a percutaneously insertable delivery element comprising a control end configured to remain outside the body and an insertion end which, when in an operative position, is configured to be adjacent to an external surface of a target portion of a lung; and
an elastic bag deployable from the distal end of the delivery element to apply compressive force to an external surface of the target portion of the lung to constrict at least one airway therein, collapsing a portion of the target portion of the lung and isolating the target portion of lung from portions of lung upstream therefrom to prevent influx of air into the target portion of lung.

2. The system of claim 1, wherein the bag comprises a band around an open end thereof which is configured to constrict around an upstream end of the target portion of the lung to prevent air flow between the target portion of the lung and remaining portions of the lung.

3. The system of claim 2, wherein the band includes one of an elastic band and a shape memory element.

4. The system of claim 2, wherein the band includes one of a tie and a clamp.

5. The system of claim 1, wherein the bag is configured so that the compressive force applied by the bag is substantially equal across a surface area of the target portion of the lung.

6. The system of claim 1, wherein the bag is configured so that the compressive force applied by the bag varies across a surface area of the target portion of the lung.

7. The system of claim 1, wherein the bag is formed of a biodegradable material.

8. The system of claim 1, wherein an elongated retractor device sized and shaped to be passed through the delivery element to deploy the bag from the distal end of the delivery element.

9. The system of claim 8, wherein a distal end of the elongated retractor device includes a plurality of arms movable between a closed position in which the arms extend toward a longitudinal axis thereof to an expanded configuration in which the arms extend radially outward to expand an opening of the bag.

10. A method for treating a respiratory condition, comprising:
inserting an insertion instrument into the thoracic cavity via an incision;
passing an elastic bag through the insertion instrument and stretching an opening of the bag to position the bag over a target portion of the lung; and
releasing the bag to apply a compressive force to an external surface of the target portion of the lung to constrict at least one airway therein, collapsing a portion of the target portion of the lung and isolating the target portion of lung from portions of lung upstream therefrom to prevent influx of air into the target portion of lung.

11. The method of claim 10, wherein the bag comprises a band around an open end thereof which constricts around an upstream end of the target portion of the lung to prevent air flow between the target portion of the lung and remaining portions of the lung.

12. The method of claim 11, wherein the band includes one of an elastic band and a shape memory element.

13. The method of claim 11, further comprising tightening a locking mechanism of the band, the band including one of a tie and a clamp.

14. The method of claim 11, wherein the bag is passed through the insertion instrument via an elongated retractor device sized and shaped to be passed through the delivery element to deploy the bag from the distal end of the delivery element.

15. The method of claim 14, further comprising moving a plurality of arms of the retractor device from a closed position in which the arms extend toward a longitudinal axis thereof to an expanded configuration in which the arms extend radially outward to stretch the opening of the bag.

16. The method of claim 10, wherein the compressive force applied by the bag is substantially equal across a surface area of the target portion of the lung.

17. The method of claim 10, wherein the compressive force applied by the bag varies across a surface area of the target portion of the lung.

18. The method of claim 10, wherein the bag is formed of a biodegradable material.

* * * * *